United States Patent
Berge et al.

(10) Patent No.: US 6,596,233 B2
(45) Date of Patent: Jul. 22, 2003

(54) AUTOMATED SANITIZING SYSTEM FOR VACUUM ICE CONVEYANCE SYSTEMS

(75) Inventors: J. Eric Berge, Irvine, CA (US); David W. Goff, San Antonio, TX (US); Raymond A. Glatt, San Antonio, TX (US)

(73) Assignee: Lancer Partnership, Ltd., San Antonio, TX (US)

( * ) Notice: Subject to any disclaimer, the term of this patent is extended or adjusted under 35 U.S.C. 154(b) by 0 days.

(21) Appl. No.: 09/804,285

(22) Filed: Mar. 12, 2001

(65) Prior Publication Data

US 2002/0127140 A1 Sep. 12, 2002

(51) Int. Cl.⁷ .............................. A61L 2/18; F28G 9/00
(52) U.S. Cl. ............................ 422/28; 422/292; 62/303
(58) Field of Search ...................... 422/28, 261, 212; 62/303, 344, 398, 400; 510/199, 195

(56) References Cited

U.S. PATENT DOCUMENTS

| | | | | |
|---|---|---|---|---|
| 4,135,947 A | * | 1/1979 | Rink | .............................. 134/4 |
| 4,389,794 A | * | 6/1983 | Bitterly | ............................. 34/5 |
| 5,077,007 A | * | 12/1991 | Pearson | ............................. 422/3 |
| 5,458,851 A | * | 10/1995 | Schroeder et al. | ............. 422/28 |
| 5,580,521 A | * | 12/1996 | Gagne | ............................ 422/28 |
| 5,581,982 A | * | 12/1996 | Schroeder et al. | ............. 53/459 |
| 6,056,885 A | * | 5/2000 | Wasinger | ................... 422/28 X |
| 6,209,339 B1 | * | 4/2001 | Schroeder et al. | ............. 63/303 |

* cited by examiner

Primary Examiner—Elizabeth McKane
(74) Attorney, Agent, or Firm—Christopher L. Makay

(57) ABSTRACT

An automated sanitizing system for a vacuum ice conveyance system generally includes a source of sanitizing solution, a source of ice, an ice hopper for association of the sanitizing solution with the ice and an outlet from the ice hopper for introduction of the association of solution and ice into a vacuum ice conveyance system. The sanitizing solution is produced at the ice hopper by mixing a concentrated sanitizing agent with water, whereafter the solution is sprayed over a harvest of ice as the ice is dropped into the hopper for conveyance through the vacuum ice conveyance system. The system is also adapted to associate clean water with the ice for rinsing from the conveyance system of the sanitizing agent.

21 Claims, 4 Drawing Sheets

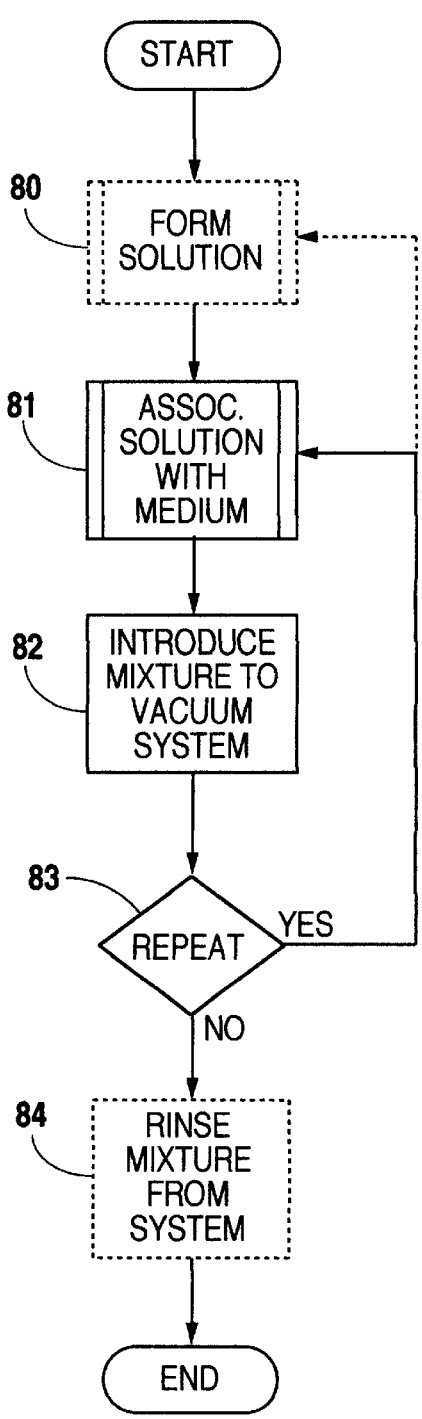
Fig. 4
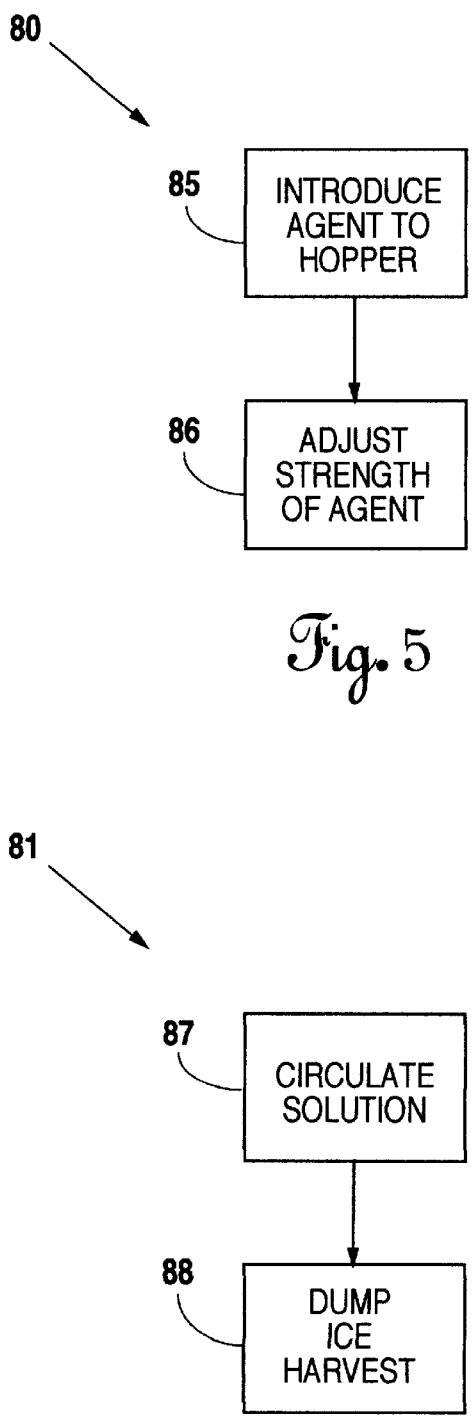
Fig. 5
Fig. 6

AUTOMATED SANITIZING SYSTEM FOR VACUUM ICE CONVEYANCE SYSTEMS

FIELD OF THE INVENTION

The present invention relates to vacuum ice conveyance systems. More particularly, the invention relates to an automated sanitizing system whereby a vacuum pneumatic ice conveyance system may be efficiently and effectively sanitized on a periodic basis.

BACKGROUND OF THE INVENTION

As shown in the exemplary embodiment of FIG. 1, vacuum ice conveyance systems 30 have been developed for the automated conveyance of ice cubes, wedges, chunks, pieces and the like 31 from an ice source 50 to one or more ice receptors 40. As described in PCT International publication No. WO 00/08396 published Feb. 17, 2000, which by this reference is incorporated herein as though now set forth in its entirety, such vacuum ice conveyance systems 30 generally comprise a vacuum source 35 for entraining ice cubes 31 through an ice conduit 32.

As shown in FIG. 1, a vacuum pump 36, or substantially equivalent source of negative pressure, draws a flow of air through an air inlet 33 at the ice source 50, into the ice conduit 32 and through a vacuum line 37 interposed in fluid communication between the fluid conduit 32 and the vacuum pump 36. The excess air drawn through the system 30 may then be exhausted through a provided vent 38. The produced air flow 46 causes the ice cubes 31 to be drawn from the ice source 50 and into the ice conduit 32, thereby establishing an ice flow 45 through the ice conduit 32. As shown in the figure, the vacuum line 37 is arranged with the ice conduit 32 just upstream from the ice receptors 40 such that the momentum of the ice flow 45 causes the ice cubes 31 to flow past the vacuum line 37 and into a provided conduit extension 39 connecting the ice conduit 32 to the desired ice receptor 40.

As described in PCT International publication No. WO 00/08396, exemplary ice receptors 40 may comprise an ice dispenser 41, an ice and beverage dispenser, an ice accumulator 42, an air lock device 43 with air inlet 44 for further automated conveyance of the ice cubes 31 or any substantial equivalent thereof. As also described in the PCT International publication, a microbial filter 34 may be provided at the air inlet 33 to the ice source 50 and/or the air inlet 44 to an implemented air lock device 43 for minimizing the introduction of airborne microbial contaminants.

Unfortunately, the implementation of such filters 34 is generally insufficient for maintaining the internal cleanliness of the vacuum ice conveyance system 30. As a result, it is necessary to chemically sanitize the vacuum ice conveyance system 30 on a periodic basis. In the past, this has required the manual introduction of cleansing solutions to the vacuum ice conveyance system 30, which has required significant labor investment and down time for the system 30. It is therefore an overriding object of the present invention to provide an apparatus and method by which such a vacuum ice conveyance system 30 may be efficiently and effectively sanitized without unnecessary disruption of the system's operation and/or additional labor investment.

SUMMARY OF THE INVENTION

In accordance with the foregoing objects, the present invention—an automated sanitizing system for a vacuum ice conveyance system—generally comprises a source of sanitizing solution, a source of solid media, a chamber for association of the sanitizing solution with the solid media and an outlet from the chamber for introduction of the association of solution and media into a vacuum ice conveyance system. Preferably the solid media comprises ice produced by an ice maker and deposited into an ice hopper, which serves as both the chamber for association of the solution with the ice and as the point of introduction to the vacuum ice conveyance system of the association. The sanitizing solution is preferably produced at the ice hopper by mixing a concentrated sanitizing agent with water, whereafter the solution is sprayed over a harvest of ice as the ice is dropped into the hopper for conveyance through the vacuum ice conveyance system. The system is also adapted to associate clean water with the ice for rinsing from the conveyance system of the sanitizing agent.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein:

FIG. 4 shows, in flowchart, the preferred method of operation of the sanitizing system of FIG. 2;

FIG. 5 shows, in flowchart, details of the preferred implementation of one step of the method of FIG. 4; and FIG. 6 shows, in flowchart, details of the preferred implementation of another step of the method of FIG. 4.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 2:
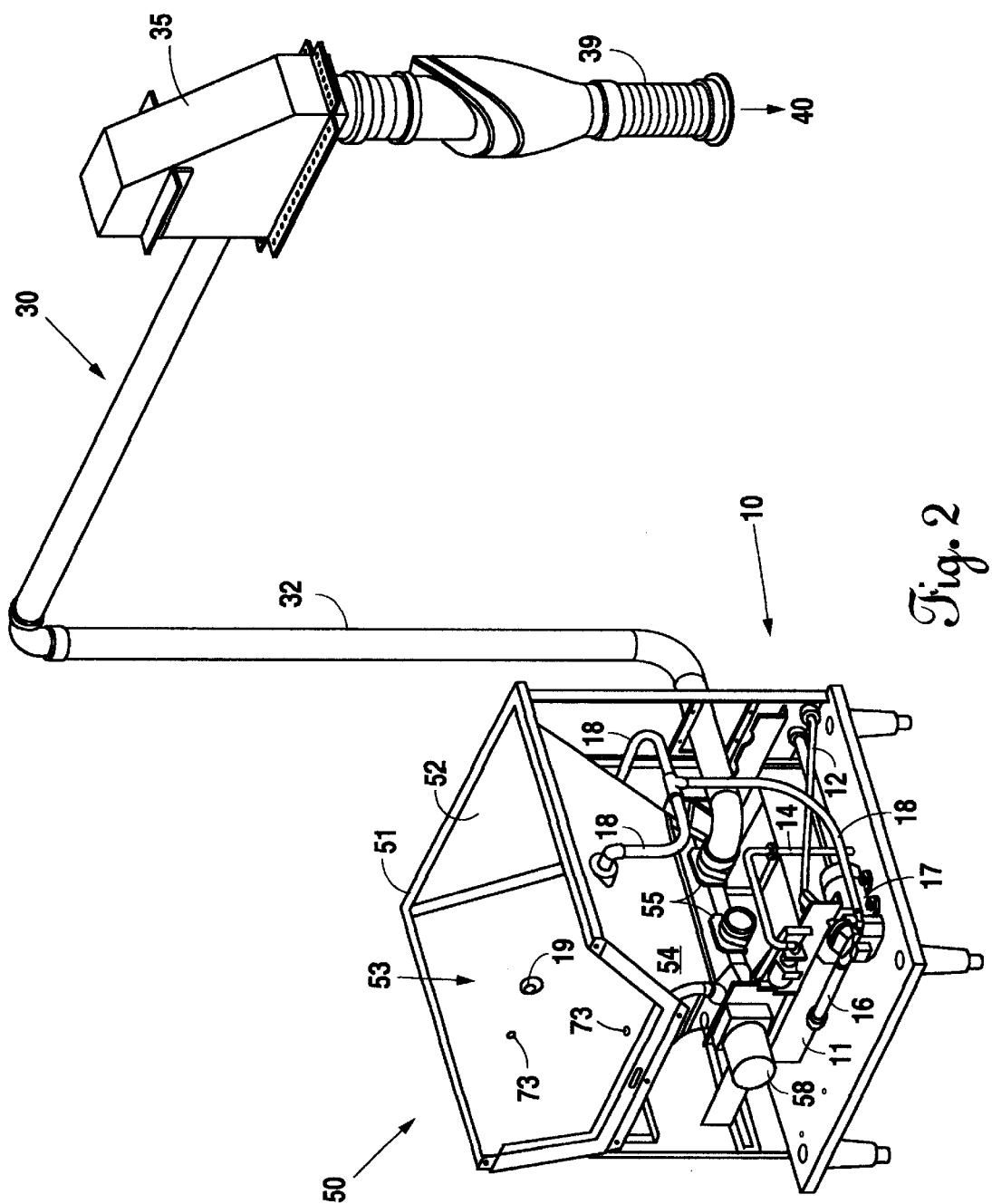
FIG. 2 shows, in perspective view, an implementation of the automated sanitizing system of the present invention as specifically adapted for use with such systems exemplified by FIG. 1.
Figure 3:
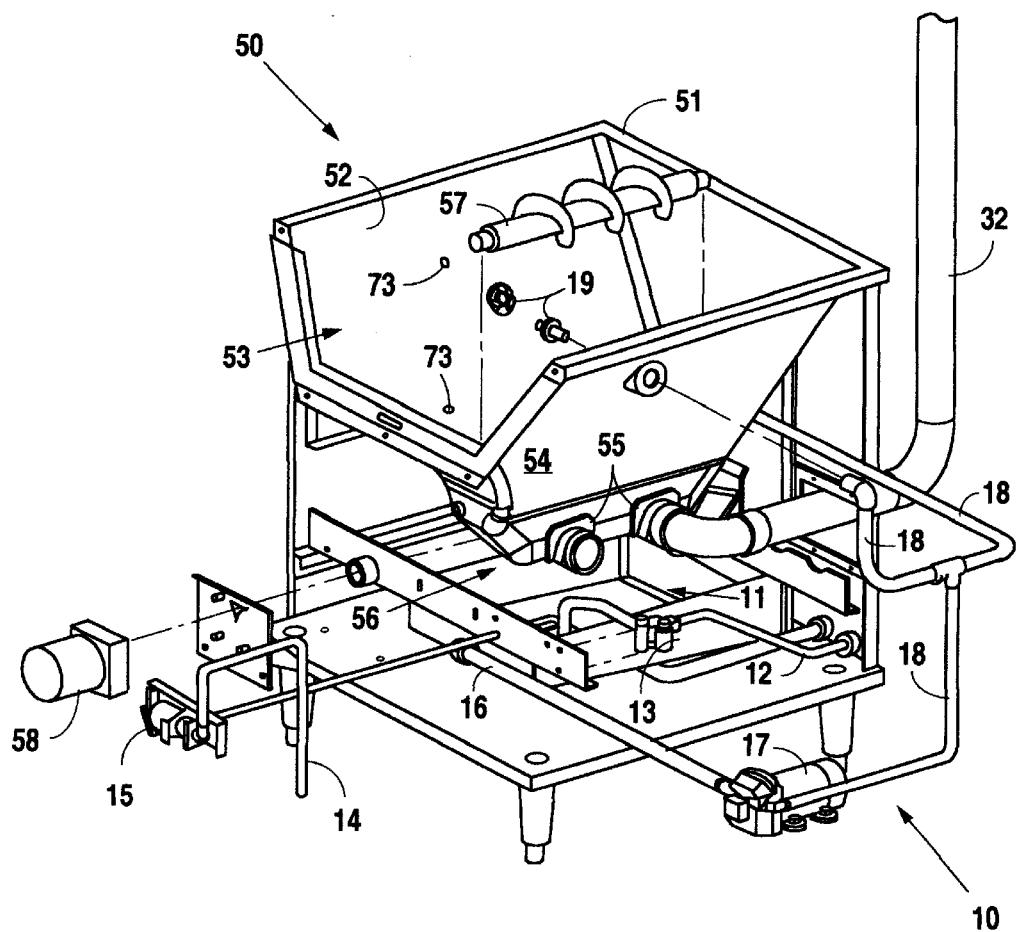
FIG. 3 shows, in partially exploded perspective view, the automated sanitizing system of FIG. 2.

Referring now to FIGS. 2 and 3, in particular, the preferred embodiment of the automated sanitizing system 10 as implemented for use with a vacuum ice conveyance system 30 is detailed. Although those of ordinary skill in the art will recognize that the automated sanitizing system 10 may be integrated with any of a variety of ice sources, the exemplary embodiment shown integrates the automated sanitizing system 10 with an ice source 50 adapted to dispense ice cubes 31 into a hopper 51. As shown in the figures, one or more ice effluents 55 at the base 54 of the hopper 51 are provided for the conveyance of ice cubes 31 into the vacuum ice conveyance system 30 with the aid of an auger 57 powered by an auger motor 58. As will be better understood further herein, the auger 57 also serves to associate a sanitizing solution with the ice cubes 31 for disinfecting the vacuum ice conveyance system 30.

As particularly shown in the partially exploded view FIG. 3, a liquid collection reservoir 11 is provided beneath the hopper 51 for the collection of liquids drained from the hopper 51 through an outlet 56 at the base 54 of the hopper 51. A collection line 16 in fluid communication with a drain channel (not shown) in the base of the liquid collection reservoir 11 provides a conduit for pumping of fluids from the liquid collection reservoir 11 through a re-circulation pump 17 and into one or more re-circulation lines 18. Each re-circulation line 18 terminates in a spray nozzle 19 arranged to spray fluids pumped through the re-circulation lines 18 about the interior faces 52 and entire interior volume 53 of the hopper 51.

The automated sanitizing system 10 of the preferred embodiment further comprises a water line 12 from a water source (not shown) to the liquid collection reservoir 11 through a provided solenoid valve 13 or the substantial equivalent thereof. Likewise, a sanitizing agent line 14 is provided for communication of a sanitizing agent, which is any agent suitable for killing microbiologicals, such as, for example, chlorine bleach, ozone, and the like, from a source thereof to the liquid collection reservoir 11 through a provided pump 15. As will be recognized by those of ordinary skill in the art, the liquid collection reservoir 11 is thus adapted to serve also as a mixing pan for the production of a sanitizing solution comprising a mixture of water and the sanitizing agent.

In operation, as detailed in FIGS. 4 through 6, periodic cleansing of the vacuum ice conveyance system 30 is achieved by first producing the desired quantity and strength of sanitizing solution in the liquid collection reservoir 11 (step 80 in FIG. 4). According to the preferred embodiment, a 200 parts per million strength solution of chlorine bleach and water is produced by pumping the necessary and sufficient quantity of chlorine bleach through the sanitizing agent line 14 (step 85 in FIG. 5) while activating the solenoid valve 13 to allow the inflow of the necessary and sufficient quantity of water through the water line 12 (step 86 in FIG. 5). After a sufficient quantity of sanitizing solution is produced, the re-circulation pump 17 is activated to pump sanitizing solution through the re-circulation lines 18 and into and about the hopper 51 (step 87 in FIG. 6) while dumping a harvest of ice therein (step 88 in FIG. 6). In this manner, the ice harvest becomes coated and intimately associated with the sanitizing solution (step 81 in FIG. 4).

In order to effect cleansing of the vacuum ice conveyance system 30, the auger 57, which serves also to facilitate the association of the sanitizing solution with the ice cubes 31, is activated concurrently with the vacuum pump 36 of the vacuum ice conveyance system 30. Ice cubes 31 are thereby drawn into the ice conduit 32 and directed through the vacuum ice conveyance system 30 along with the re-circulated sanitizing solution (step 82 in FIG. 4). Although those of ordinary skill in the art will recognize that the sanitizing solution could be drawn into the vacuum ice conveyance system 30 without any ice cubes 31 present, Applicant has found that the simultaneous conduction of the ice cubes 31 and sanitizing solution through the vacuum ice conveyance system 30 serves to agitate and foam the sanitizing solution. In this manner, complete contact with the interior spaces of the vacuum ice conveyance system 30 is achieved, thereby resulting in more effective cleansing than is possible without the ice cubes 31. Because conduction of a liquid only through the vacuum ice conveyance system 30 generally follows distinct pathways through the ice conduit 32, especially in horizontally oriented regions of the ice conduit 32, the mixture of the sanitizing solution with a solid medium, such as the ice cubes 31, is considered a critical aspect of the present invention.

Upon conduction of the ice cube 31 and sanitizing solution mixture through the vacuum ice conveyance system 30, the process may be repeated if desired to ensure complete sanitization or for conduction of the produced mixture through portions of a multi-conduit vacuum ice conveyance system 30 closed during earlier cleaning cycles (step 83 in FIG. 4). In any case, it is desired that the sanitizing solution be rinsed from within the vacuum ice conveyance system 30 following its conduction therethrough (step 84 in FIG. 4). To this end, clean water is introduced to the liquid collection reservoir 11 through the water line 12 without the introduction thereto of the sanitizing agent 14. The water is then pumped by the re-circulation pump 17 through the re-circulation lines 18 and into and over a subsequent, clean harvest of ice cubes 31. The clean water and ice cube 31 mixture is then conveyed through the vacuum ice conveyance system 30 in similar fashion to that previously described.

Figure 1:
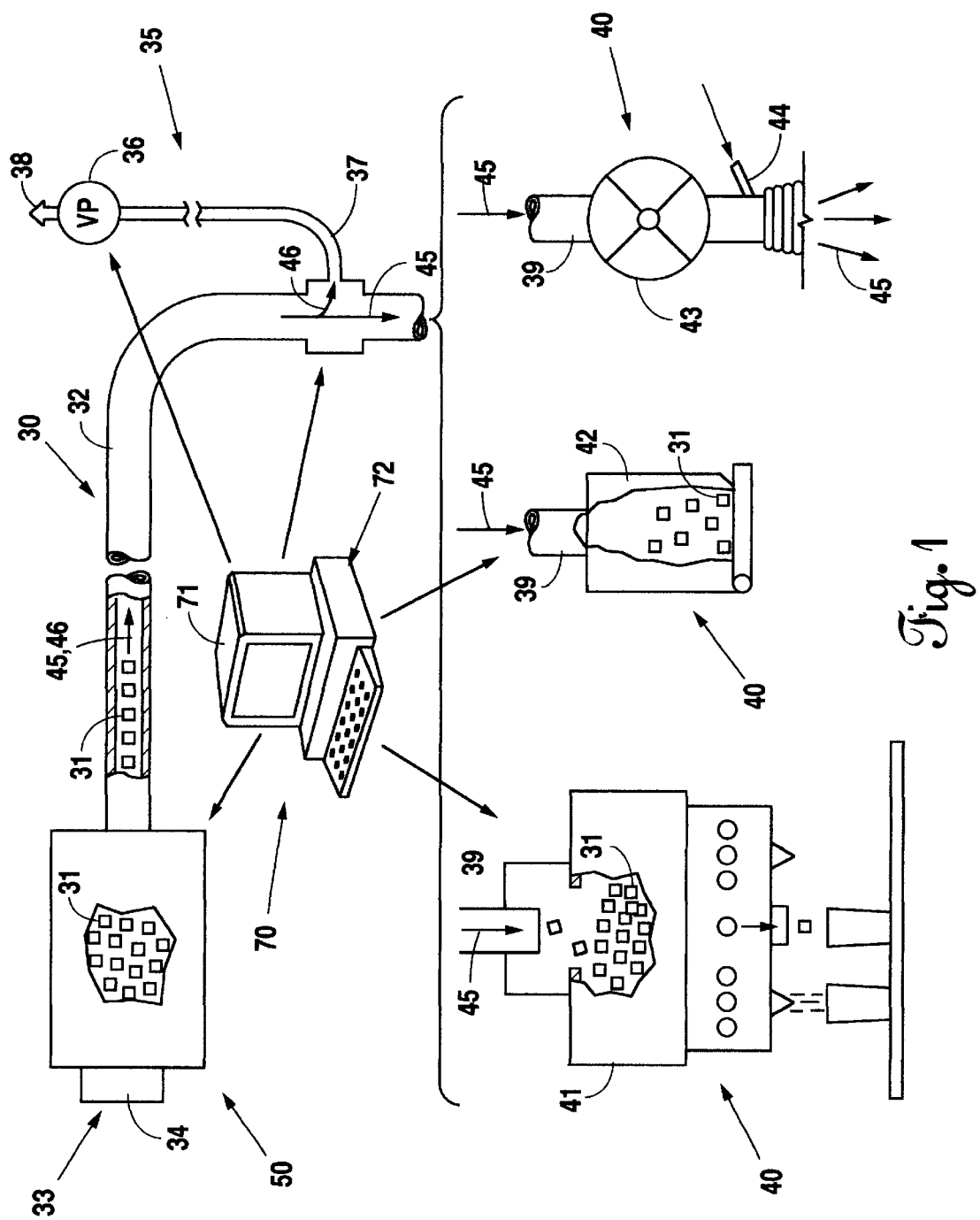
FIG. 1 shows, in functional block diagrams, a vacuum pneumatic ice conveyance system as typically implemented in the art.

Finally, as shown particularly in FIG. 1, known vacuum ice conveyance systems 30 generally comprise an electronic controller 70 such as a computer 71 provided with appropriate custom or conventional software 72. It is considered within the realm of those of ordinary skill in the art to implement the necessary timing and control algorithms for the operation of the automated sanitizing system 10 within the provided electronic controller 70. Those of ordinary skill in the art will recognize, however, that a separate controller may also be provided and interfaced with the electronic controller 70 of the vacuum ice conveyance system 30, as necessary.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, ice level sensors 73, such as photo-detector and emitter pairs, may be integrated with the automated sanitizing system 10 for ensuring that all ice cubes 31 that have been sprayed with sanitizing solution are completely removed from the hopper 51 before ice cubes 31 for human consumption are reintroduced thereto. The details of such an extension are readily within the ordinary skill in the art.

Likewise, those of ordinary skill in the art will recognize that solid media other than ice cubes 31 may be utilized to produce the desired agitation of the sanitizing solution. Ice cubes 31 are preferred, however, as they are readily available, effectively produce the desired result, and may be easily removed from the ultimate ice receptors 40 by the flushing of water through the vacuum ice conveyance system 30, thereby causing them to melt.

Additionally, those of ordinary skill in the art will recognize that many alternative arrangements for the production of the sanitizing solution and its introduction to the vacuum ice conveyance system 30 may be implemented. Although in no way limiting of the present invention, several such arrangements are described in detail in U.S. Pat. No. 5,458,851 issued Oct. 17, 1995 to Schroeder et al. By this reference, the full disclosure of U.S. Pat. No. 5,458,851 is incorporated herein as though now set forth in its entirety. Likewise, those of ordinary skill in the art will recognize that the solution forming step 80 may be omitted by providing access to a dilute solution, the disadvantage associated therewith being the necessity to handle large quantities of pre-made solution.

In any case, because the scope of the present invention is much broader than any particular embodiment, the foregoing detailed description should not be construed as a limitation of the scope of the present invention, which is limited only by the claims appended hereto.

What is claimed is:

1. An automated sanitizing system for a vacuum ice conveyance system, said automated sanitizing system comprising:
    an ice hopper for association of a sanitizing solution with ice disposed therein;
    a source of sanitizing solution, said source of sanitizing solution being in communication with said ice hopper;
    a source of ice, said source of ice being in communication with said ice hopper; and
    an outlet from said ice hopper, said outlet being adapted to insert said sanitizing solution with said ice into the vacuum ice conveyance system.

2. The automated sanitizing system as recited in claim 1, wherein said source of sanitizing solution comprises a sanitizing agent line having a first end originating in fluid communication with a source of sanitizing agent and a second end terminating in the proximity of said ice hopper.

3. The automated sanitizing system as recited in claim 2, wherein said source of sanitizing solution further comprises a pump, said pump being interposed said first end and said second end of said sanitizing agent line for delivery of the sanitizing agent to said ice hopper.

4. The automated sanitizing system as recited in claim 2, wherein said source of sanitizing solution further comprises a water line from a source of water, said water line terminating in the proximity of said ice hopper.

5. The automated sanitizing system as recited in claim 4, wherein said source of sanitizing solution further comprises a valve in said water line for controlling the flow of water therethrough.

6. The automated sanitizing system as recited in claim 5, wherein said valve comprises a solenoid controlled valve.

7. The automated sanitizing system as recited in claim 4, wherein said ice hopper comprises at least one re-circulation line, said re-circulating line originating in a liquid collection reservoir of said ice hopper and terminating in the proximity of an upper portion of said ice hopper.

8. The automated sanitizing system as recited in claim 7, wherein said ice hopper further comprises a re-circulation pump for pumping fluids through each said re-circulation line.

9. The automated sanitizing system as recited in claim 8, wherein each said re-circulation line terminates in a spray nozzle, each said spray nozzle being adapted to direct fluids pumped through a respective re-circulation line over said ice hopper.

10. The automated sanitizing system as recited in claim 8, wherein said source of ice comprises an ice maker.

11. The automated sanitizing system as recited in claim 10, wherein said outlet comprises an ice effluent.

12. The automated sanitizing system as recited in claim 11, wherein said outlet further comprises an auger for directing ice into said ice effluent.

13. The automated sanitizing system as recited in claim 11, said automated sanitizing system further comprising a controller, said controller being adapted to:
    control flows through said sanitizing agent line and said water line to form a sanitizing solution;
    control flows through said re-circulation line to associate said sanitizing solution with said ice, thereby forming a mixture of said sanitizing solution and said ice; and
    control flows through said ice effluent to introduce said mixture to the vacuum ice conveyance system.

14. A method for sanitizing a vacuum ice conveyance system, said method comprising the steps of:
    providing a sanitizing solution;
    providing solid media;
    associating said sanitizing solution with said solid media, thereby forming a mixture of sanitizing solution and solid media; and
    introducing said mixture into the vacuum ice conveyance system.

15. The method as recited in claim 14, wherein said solid media comprises ice.

16. The method as recited in claim 14, wherein said providing a solid media step comprises harvesting a crop of ice into an ice hopper.

17. The method as recited in claim 16, wherein said associating step comprises spraying said sanitizing solution over said solid media.

18. The method as recited in claim 17, wherein said associating step further comprises re-circulating said sanitizing solution over said solid media.

19. The method as recited in claim 17, wherein said providing a sanitizing solution step comprises mixing a concentrated sanitizing agent with water to form a dilute sanitizing solution.

20. The method as recited in claim 17, said method further comprising the step of rinsing said mixture from the vacuum ice conveyance system.

21. The method as recited in claim 20, wherein said rinsing said mixture step comprises the steps of:
    providing water;
    providing a solid media;
    associating said water with said solid media, thereby forming a water mixture of water and solid media; and
    introducing said water mixture into the vacuum ice conveyance system.

* * * * *